United States Patent [19]
Lussow et al.

[11] Patent Number: 6,013,641
[45] Date of Patent: Jan. 11, 2000

[54] USE OF HYALURONIC ACID AS AN IMMUNOSUPPRESSANT

[75] Inventors: Alexander R. Lussow, Menlo Park; Roland Buelow, Palo Alto, both of Calif.

[73] Assignee: SangStat Medical Corporation, Fremont, Calif.

[21] Appl. No.: 08/721,835

[22] Filed: Sep. 27, 1996

Related U.S. Application Data

[60] Provisional application No. 60/004,468, Sep. 28, 1995.

[51] Int. Cl.$^7$ .................................................. A01N 43/04
[52] U.S. Cl. ............................................................ 514/54
[58] Field of Search ........................ 514/53, 54; 424/422, 424/444, 457, 461, 488

[56] References Cited

U.S. PATENT DOCUMENTS 5,356,883 10/1994 Kuo et al. .................................. 514/54

FOREIGN PATENT DOCUMENTS

| 0 656 213 | 6/1995 | European Pat. Off. . |
| 87/05517 | 9/1987 | WIPO . |
| 9104058 | 4/1991 | WIPO . |
| 93/16733 | 9/1993 | WIPO . |

OTHER PUBLICATIONS

Chevrier et al., "Inhibition of active E rosette forming T lymphocytes by hyaluronic acid—evidence of a receptor for hyaluronic acid on a lymphocyte subpopulation", Biomedicine 1982; 36:100–103, 1982.

Angeleri, M.L., et al., "Terapia Immunosoppressiva Nella Prevenzion Del Rigetto Del Trapianto Corneale", *Arch. Med. Interna.*, 43(2):81–85 (1991).

Gowland, G. et al., "Marked Echanced Efficacy of Cyclosporin When Combined With Hyaluronic Acid", *Clin. Drug Invest.* 11(4):245–250 (1996).

Bartolazzi, A. et al., "Interaction between CD44 and Hyaluronate is Directly Implicated in the Regulation of Tumor Development," *J. Exp. Med.*, 180:53–66 (1994).

Knudson, C.B. and W. Knudson, "Hyaluronan–Binding Proteins in Development, Tissue Homeostasis, and Disease," *The FASEB Journal*, 7(13) : 1233–1239 (1993).

Delfino, D.V. et al. "Role of CD44 in the Development of Natural Killer Cells from Precursors in Long–Term Cultures of Mouse Bone Marrow," *Journal of Immunology*, 152(11):5171–5179 (1994).

Lesley, J. et al., "Hyaluronan Binding Function of CD44 is Transiently Activated on T Cells During an In Vivo Immune Response," *J. Exp. Med.*, 180:383–387 (1994).

Kimura, K. et al., "Role of Glycosaminoglycans in the Regulation of T Cell Proliferation Induced by Thymic Stroma–Derived T Cell Growth Factor," *The Journal of Immunology*, 146:2618–2624 (1991).

Galdandrini, R. et al., "Hyaluronate is Costimulatory for Human T Cell Effector Functions and Binds to CD44 on Activated T Cells," *The Journal of Immunology*, 153:21–31 (1994).

Funaro, A. et al., "Stimulation of T Cells Via CD44 Requires Leukocyte–Function–Associated Antigen Interactions and Interleukin–2 Production," *Human Immunology*, 40:267–278 (1994).

*Primary Examiner*—Donna Wortman
*Assistant Examiner*—Brenda G. Brumback
*Attorney, Agent, or Firm*—Richard F. Trecartin; Todd A. Lorenz; Albritton & Herbert LLP

[57] ABSTRACT

A pharmaceutical formulation of hyaluronic acid is administered to a patient suffering from undesirable T cellactivity. The hyaluronic acid inhibits T cell activity at doses that are well-tolerated by the recipient. Conditions suitable for treatment include graft vs. host disease, graft rejection and certain autoimmune diseases having a T cell component.

11 Claims, 2 Drawing Sheets

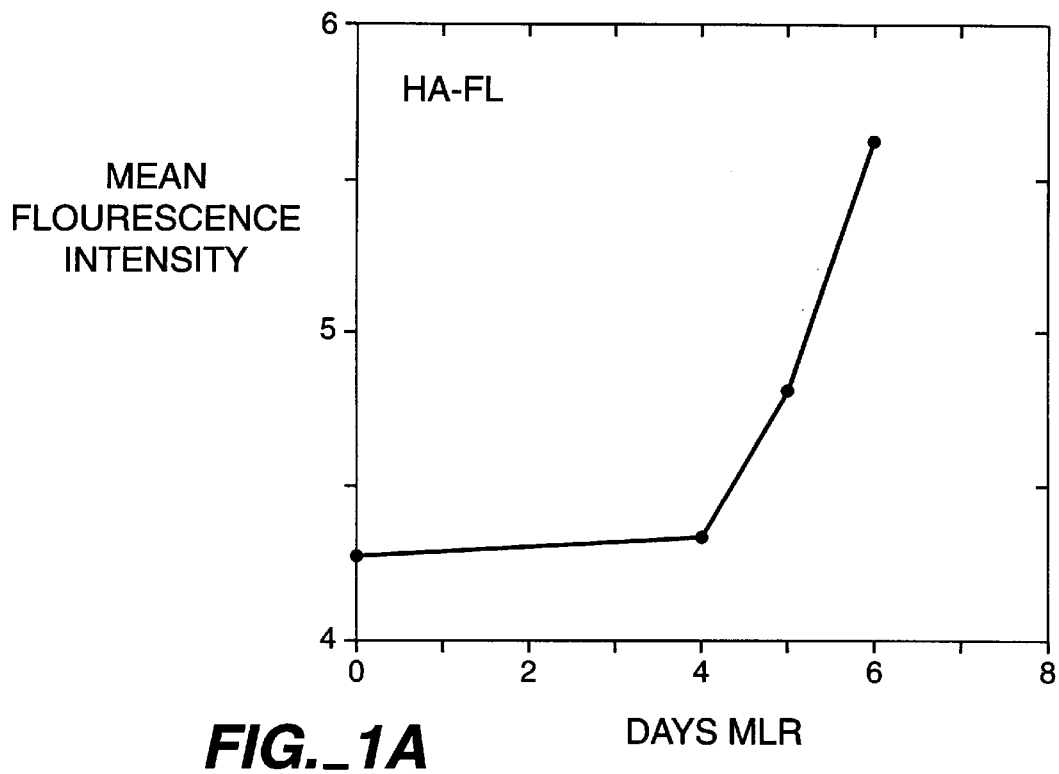
FIG._1A
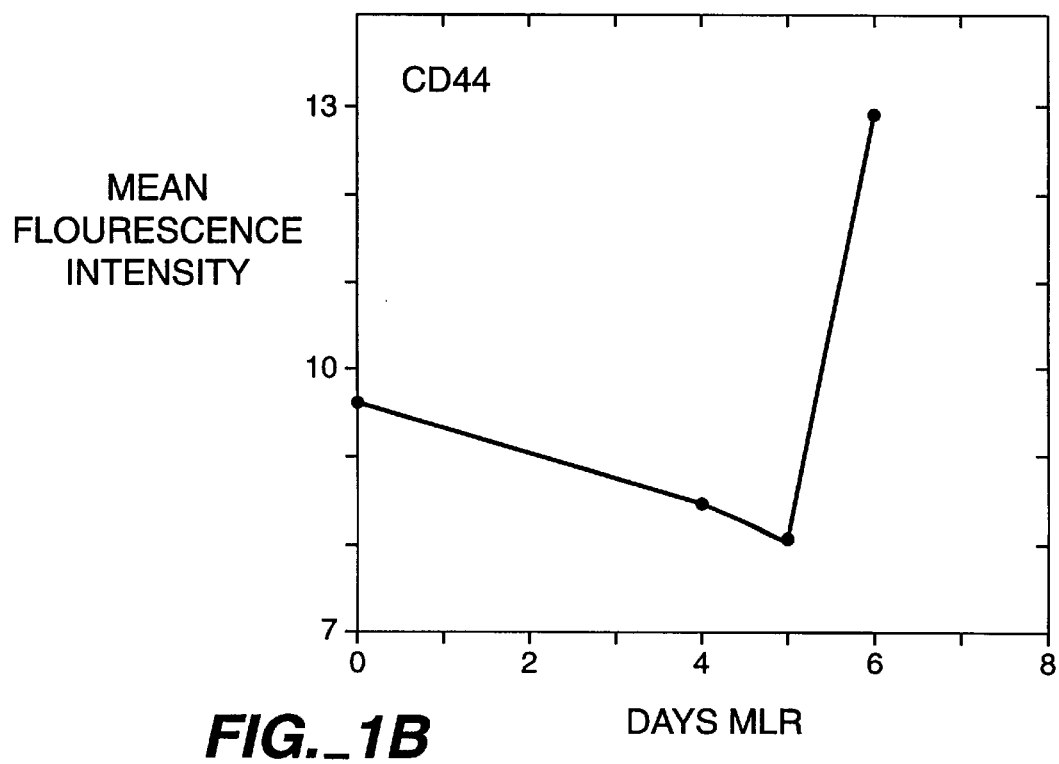
FIG._1B

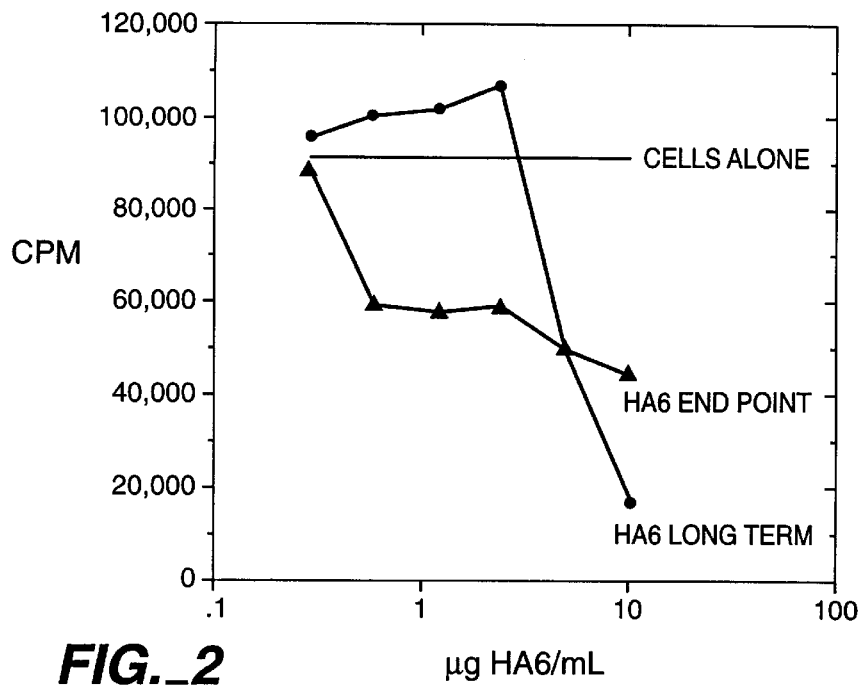
FIG._2
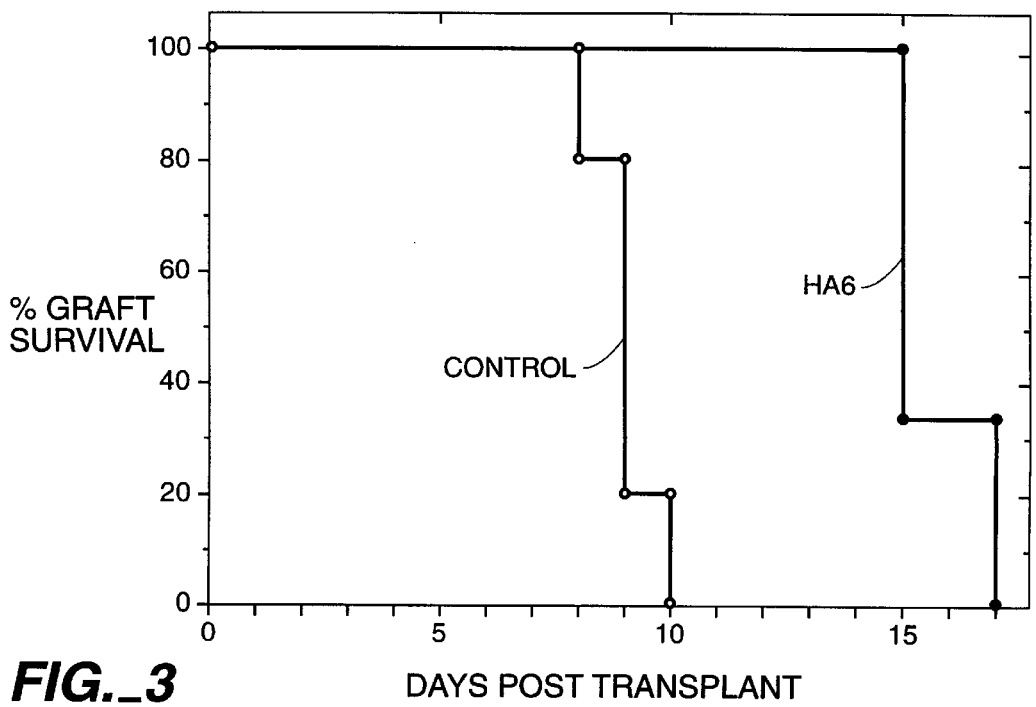
FIG._3

USE OF HYALURONIC ACID AS AN IMMUNOSUPPRESSANT

The present application claims priority to provisional application Ser. No. 60/004,468, filed Sep. 28, 1995, now abandoned.

TECHNICAL FIELD

The field of this invention is methods of immunosuppression.

BACKGROUND

Hyaluronic acid (HA) is a naturally occurring, high molecular weight polymer of repeating D-glucuronic β (1–3) N-acetyl-D-glucosamine disaccharide subunits. The native forms are indeterminate in length. The structure of the molecule has been conserved throughout evolution, and is virtually identical between species. Due to its carbohydrate composition and ubiquitous distribution, most animals are immunologically tolerant of it Several commercial uses of hyaluronic acid have been developed. These include using the natural water retention capacity of HA to maintain ocular fluid or to lubricate defective joints, employing the net-like structure of high molecular weight HA to capture drugs and carry them to the site of tissue damage, and blocking the metastases of HA binding tumor cells.

Hyaluronic acid is a ligand for a number of cell surface and extracellular matrix proteins, including ICAM-1 and CD44. Through these and other binding proteins, HA has been implicated in tumor metastasis, inflammation, cell division, wound healing, tissue hydration, and other biological functions.

Complex immune systems must achieve a delicate balance, where pathogens are recognized and eliminated, but host cells are safe from immune destruction. One mechanism for immune recognition is the expression of major histocompatibility complex proteins on the cell surface. These highly polymorphic proteins are a means of identifying cells as "self" or "foreign". During tissue transplantation, it is rare to find a perfect match between donor and host MHC antigens. The host immune system is therefore activated, and some level of immunosuppression is required to prevent graft rejection.

Immunosuppressants such as cyclosporin A, FK506, rapamycin and azathioprine have been used to prevent graft rejection, and to treat some forms of autoimmune disease. However, they have numerous side effects. There is therefore substantial interest in identifying new agents that can inhibit the activation of specific cells, particularly T cells, while having fewer side effects.

Relevant Literature

Bartolazzi et al. (1994) *J. Exp. Med.* 180:53–66 describes the interaction between CD44 and hyaluronate in the regulation of tumor development. The role of hyaluran-binding proteins in development, tissue homeostasis and disease is discussed in Knudsen and Knudsen (1993) *FASEB J.* 7:1233–1241.

Delfino et al. (1994) *J Immunol* 152:5171–9 discloses the role of CD44 in the development of natural killer cells from precursors in long-term cultures of mouse bone marrow. Lesley et al. (1994) *J. Exp. Med.* 180:383–387 finds that hyaluran binding function of CD44 is transiently activated on T cells during an in vivo immune response. The role of glycosaminoglycans in the regulation of T cell proliferation induced by thymic stroma-derived T cell growth factor is discussed in Kimura et al. (1991) *J Immunol* 146:2618–24. It is found that heparin and heparin sulfate inhibit T cell proliferation in the experimental system, but hyaluronic acid had no effect.

Galandrini et al. (1994) *J Immunol* 153:21–31 describes co-stimulation of human T cell effector functions with hyaluran. Funaro et al. (1994) *Hum. Immunol.* 40:267–78 discloses that stimulation of T cells via CD44 requires leukocyte-function-associated antigen interactions and interleukin-2 production.

Hyaluronic acid has been used as a carrier for drug delivery, described in U.S. Pat. No. 5,256,411 and International patent applications WO 91/04058 and WO 93/16733. Specific examples for ocular use are described in U.S. Pat. Nos. 4,839,342 and 5,411,952. U.S. Pat. No. 4,725,585 discloses the use of HA to normalize granulocytic phagocyte activity.

SUMMARY OF THE INVENTION

Methods are provided for inhibiting T cell activity. A pharmaceutical formulation of a polymeric D-glucuronic β (1–3) N-acetyl-D-glucosamine disaccharide, e.g. hyaluronic acid (HA), is systemically administered to a patient. The methods are effective for reducing graft rejection, and for inhibiting other undesirable T cell activity. The formulation may optionally include other immunosuppressive compounds.

BRIEF DESCRIPTION OF THE DRAWINGS

FIG. 1A is a graph showing the kinetics of hyaluronic acid binding to T cells following activation by mixed lymphocyte reaction (MLR) using mitomycin C inactivated C57BL/6 lymph node cells as stimulators and BALB/c cells as responders. FIG. 1B shows the same cells stained with an antibody specific for CD44.

FIG. 2 is a graph depicting the uptake of $^3$H-thymidine by cells in a mixed lymphocyte reaction. Cells were either incubated with serial dilutions of hyaluronic acid over the entire 5 day period of stimulation (▲: long term), or with hyaluronic acid added 24 hrs prior to harvesting the cells (●: end point), or without any additive (no symbol).

FIG. 3 is a graph showing survival of a cardiac graft where the recipients received no additional treatment (○), or daily injections of HA6 (●: 1.5 mg/Kg/day) administered via the tail vein.

DESCRIPTION OF THE SPECIFIC EMBODIMENTS

Hyaluronic acid (HA) is systemically administered to a mammalian host in a dose sufficient to inhibit undesirable T cell activity. The hyaluronic acid is effective at doses that are well-tolerated by the host animal. The disorders that may be treated by this method include graft rejection, T cell mediated pathology, e.g. delayed type hypersensitivity and T cell mediated autoimmune conditions.

Hyaluronic acid is a naturally occurring, high viscosity mucopolysaccharide with repeating D-glucuronic β (1–3) N-acetyl-D-glucosamine disaccharide subunits. For use in the subject methods, HA may be synthesized, or isolated from various natural sources, as known in the art. See, for example U.S. Pat. No. 4,141,973. The HA polymer will be at least two disaccharide subunits in length (HA2), more usually at least about 6 subunits in length (HA6) and may be as many as 80 subunits (HA80), more usually not more than sixty (HA60). High molecular weight HA can be digested chemically or enzymatically to yield shorter fragments. The formulation may be a mixture of different molecular weight HA polymers. Alternatively, the formulation will comprise predominantly one polymer length, where at least about 60%, more usually at least about 80% by weight of the HA is one polymer length. In one embodiment of the invention, the predominant polymer will be HA6, where the remainder of polymer present will be a mixture of HA4, HA5, HA7 and HA8. The polymer may be linear, branched or stacked. Branched polymers may comprise additional linkages at the 2, 3 or 6 position of glucuronic acid, or the 3, 4 or 6 position of glucosamine. Stacked polymers may have covalent or non-covalent bonds that stabilize or cross-link complexes of multiple polymers.

The hyaluronic acid formulation will be administered at a dosage sufficient to inhibit undesirable T cell activity. The T cells may be cytotoxic, e.g. CD8+ cells, or T helper cells, e.g. CD4+. Activated T cells will be inhibited by the subject treatment to a greater extent than resting T cells. In many cases it will be desirable to inhibit the activity of cytotoxic T cells. The determination of undesirable T cell activity will vary with the condition that is being treated, e.g. graft rejection, autoimmune disease, graft versus host disease, etc. For suppression of graft rejection, T cell activity may be indirectly determined by survival of engrafted tissue, where increased graft survival correlates with decreased T cell activity. Other useful measures of T cell activity are the release of cytokines, e.g. IL-1, IL-2, IL-3, IL-4, IL-5, IL-6, IL-8, IL-9, IL-10, IL-13, IL-14, GM-CSF, IFN$\gamma$, LIF, TNF$\alpha$, TNF$\beta$; the presence of T cells at disease associated sites, e.g. islets of langerhans in diabetes, transplanted tissue, etc.; and other measures of4T cell activity as known in the art.

The level of T cell inhibition will be sufficient to reduce the severity of the disease. For example, a graft will survive at least about 25% longer when the recipient is treated with the subject HA formulation, and the graft survival may be extended by as much as 50%.

Depending on the desired use, the HA will be administered in vivo or in vitro. The dosage in vivo will vary with the patient health, the condition being treated, the desired level of inhibition, etc. Generally, the dose which is administered will be in the range of about 0.1–50, more usually from about 1–25 mg/kg, of host weight. The host may be any mammal including domestic animals, pets, laboratory animals, primates, particularly humans. The amount will generally be adjusted depending upon the physiological half life of the polysaccharide, where shorter polymers tend to have a shorter half life.

The hyaluronic acid formulation may be administered in a variety of ways, particularly systemically. For injection, the HA may be injected subcutaneously, intraperitoneally, intramuscularly, intravascularly, etc. Depending upon the manner of introduction, the compounds may be formulated in a variety of ways.

In vitro, HA is used to reduce the activity of T cells in cell cultures, as a control to study the effect of other immunosuppressants, in drug screening assays for agents that increase T cell activity, etc. Generally, the concentration of the polysaccharides will vary in the medium, depending upon the level of inhibition desired, the presence of other compounds affecting T cell activation, and the like.

By transplantation it is meant that donor tissue is joined with the graft recipient's body. Grafts include the transplantation of cells, tissues and organs, such as the transfusion of blood or blood components, the grafting of bone, skin, bone marrow, etc., and the transplantation of tissues of the eye, pancreas, liver, kidney, heart, brain, bowel, lung, etc. Of interest are transplantation of hematopoietic cells, e.g. bone marrow, mobilized hematiopietic stem cells in peripheral blood, etc., transplantation of kidneys and transplantation of hearts. As used herein, a graft recipient is an individual to whom tissue or cells from another individual (donor), commonly of the same species, has been transferred, particularly where one or more of the Class I MHC antigens are different in the donor as compared to the recipient. However, in many instances xenogeneic, e.g. pig, baboon, etc., tissue, cells or organs will be involved. The graft recipient and donor are generally mammals, preferably human.

Hyaluronic acid is effective in decreasing the adverse effects of autoimmune disease where the disease is mediated by T cells. The effect of the treatment is to spare the function of the autologous tissue which is the target of the autoreactive T lymphocytes. In addition, there may be a reduction in the inflammation, swelling, release of cytokines, perforins, granzymes, etc., which are associated with T cell activation.

The autoimmune diseases of interest will be associated with T-cell mediated tissue destruction. Included are multiple sclerosis, rheumatoid arthritis, psoriasis, pemphigus vulgaris, Sjogren's disease, thyroid disease, Hashimoto's thyroiditis, myasthenia gravis, as well as many others. Treatment of primates, more particularly humans is of interest, but other mammals may also benefit from treatment, particularly domestic animals such as equine, bovine, ovine, feline, canine, murine, lagomorpha, and the like.

The hyaluronic acid formulation will desirably be administered during the presymptomatic or preclinical stage of the disease, and in some cases during the symptomatic stage of the disease. Early treatment is preferable, in order to prevent the loss of function associated with autoimmune tissue damage. The presymptomatic, or preclinical stage will be defined as that period not later than when there is T cell involvement at the site of disease, e.g. islets of Langerhans, synovial tissue, thyroid gland, etc., but the loss of function is not yet severe enough to produce the clinical symptoms indicative of overt disease. T cell involvement may be evidenced by the presence of elevated numbers of T cells at the site of disease, the presence of T cells specific for autoantigens, the release of perforins and granzymes at the site of disease, response to immunosuppressive therapy, etc.

Human IDDM is a cell-mediated autoimmune disorder leading to destruction of insulin-secreting $\beta$ cells and overt hyperglycemia T lymphocytes invade the islets of Langerhans, and specifically destroy insulin-producing $\beta$-cells. The depletion of $\beta$ cells results in an inability to regulate levels of glucose in the blood. Overt diabetes occurs when the level of glucose in the blood rises above a specific level, usually about 250 mg/dl.

In humans a long presymptomatic period precedes the onset of diabetes. During this period there is a gradual loss of pancreatic $\beta$ cell function. The disease progression may be monitored in individuals diagnosed by family history and genetic analysis as being susceptible. The most important genetic effect is seen with genes of the major histocompatibility locus (IDDM1), although other loci, including the insulin gene region (IDDM2) also show linkage to the disease (see Davies et al, supra and Kennedy et al. (1995) *Nature Genetics* 9:293–298). Markers that may be evaluated during the presymptomatic stage are the presence of insulitis in the pancreas, the level and frequency of islet cell antibodies, islet cell surface antibodies, aberrant expression of Class II MHC molecules on pancreatic $\beta$ cells, glucose concentration in the blood, and the plasma concentration of insulin. An increase in the number of T lymphocytes in the pancreas, islet cell antibodies and blood glucose is indicative of the disease, as is a decrease in insulin concentration. After the onset of overt diabetes, patients with residual β cell function, evidenced by the plasma persistence of insulin C-peptide, may also benefit from administration of the subject polysaccharides in order to prevent further loss of function.

A quantitative increase in myelin-autoreactive T cells with the capacity to secrete IFN-gamma is associated with the pathogenesis of MS, suggesting that autoimmune inducer/helper T lymphocytes in the peripheral blood of MS patients may initiate and/or regulate the demyelination process in patients with MS. The overt disease is associated with muscle weakness, loss of abdominal reflexes, visual defects and paresthesias. During the presymptomatic period there is infiltration of leukocytes into the cerebrospinal fluid, inflammation and demyelination. Family histories and the presence of the HLA haplotype DRB1*1501, DQA1*0102, DQB1*0602 are indicative of a susceptibility to the disease. Markers that may be monitored for disease progression are the presence of antibodies in the cerebrospinal fluid, "evoked potentials" seen by electroencephalography in the visual cortex and brainstem, and the presence of spinal cord defects by MRI or computerized tomography. Treatment during the early stages of the disease will slow down or arrest the further loss of neural function.

There is significant immunological activity within the synovium during the course of the rheumatoid arthritis. This reactivity provides an intense stimulus to the synovial lining cells, which then brings about joint erosion through the release of destructive mediators. The release of cytokines, proteases and reactive oxygen intermediates have all been implicated in the disease pathology. There is increased risk of disease for persons having the HLA-Dw4 allele. While treatment with the subject polysaccharides during early stages is desirable, the adverse symptoms of the disease may be at least partially alleviated by treatment during later stages.

Administration in vivo for transplantation recipients or autoimmune disease patients may be performed as frequently as daily, or as infrequently as weekly, usually daily. Daily administrations may be one or more times, usually not more than about four times, particularly depending upon the level of drug which is administered. Treatment will be maintained as long as the T cell inhibition is desired. For transplantation recipients, the subject formulation may be administered prior to tranplantation, administration usually beginning not later than about 1 day prior to implantation. Administration may be continued on a predetermined schedule thereafter, usually not past 30 days, more usually not past 20 days. However, after implantation, the subject compositions may be administered as needed, depending upon the response of the recipient to the organ.

The hyaluronic acid may be administered as a single active agent, or in combination with other therapeutic agents, particularly other immunosuppressants. The effect of combined immunosuppressant and HA will generally be at least additive in the level of immunosuppression achieved with the single drugs, and may provide for a synergistic effect. Immunosuppressants of interest include cyclosporins A and G, FK-506, mycophenylate mofetil, rapamycin, azathioprine, antibodies for plasma membrane proteins associated with graft rejection, such as antibodies to CD4, CD8, CD2, LFA-1, ICAM-1, CD28, and the like; and immunosuppressive oligopeptides derived from MHC molecules (see, for example International application PCT/US93/01758). Antibacterial, antiviral and antifungal drugs may also be co-formulated with HA in order to minimize the effects of immunosuppression.

If administered as a single drug, the hyaluronic acid will usually comprise at least 20% by weight of the formulation, more usually at least about 75% by weight, preferably at least about 95% by weight, and for therapeutic purposes, usually at least about 99.5% by weight, in relation to contaminants related to the method of preparation of the product and its purification.

It is convenient to administer the hyaluronic acid dissolved in water and buffered to physiological pH, for example in the form of a physiologically acceptable water soluble salt, e.g. sodium, potassium, magnesium, calcium, and the like, as known in the art. Other, non-aqueous physiologically acceptable solvents may be used as necessary, particularly for combinations of active ingredients. Useful solvents include ethanol, propylene glycol, animal and vegetable oils, etc. The concentration of therapeutically active compound in the formulation may vary from about 0.5–100 wt. %.

Other agents may be employed in the formulation for a variety of purposes. For example, buffering agents and preservatives may be employed. Water soluble preservatives which may be employed include sodium bisulfite, sodium bisulfate, sodium thiosulfate, benzalkonium chloride, chlorobutanol, thimerosal, phenylmercuric acetate, phenylmercuric nitrate, methylparaben, polyvinyl alcohol and phenylethyl alcohol. These agents may be present in individual amounts of from about 0.001 to about 5% by weight and preferably about 0.01 to about 2%. Suitable water soluble buffering agents that may be employed are sodium carbonate, sodium borate, sodium phosphate, sodium acetate, sodium bicarbonate, etc., as approved by the FDA for the desired route of administration. These agents may be present in amounts sufficient to maintain a pH of the system of between 2 to 9 and preferably 4 to 8. As such the buffering agent may be as much as 5% on a weight to weight basis of the total composition.

Depending upon their intended use, particularly for administration to mammalian hosts, the subject polysaccharides may be modified to change their distribution in the blood stream, diminish or enhance binding to blood components, and the like. The subject polysaccharides may also be combined with proteins such as an antibody, where the antibody is specific for the transplanted organ, thereby targeting the drug to the tissue of interest. The subject polysaccharides may be bound to these other components by linkers which are covalent or non-covalent, and may be cleavable or non-cleavable in the physiological environment of the blood.

An antibody complex of interest utilizes hapten specific antibodies and hapten conjugated hyaluronic acid. The hapten specific antibodies will usually have an affinity of at least about 100 μM for the hapten. Preferred antibodies are syngeneic for the host. For the treatment of human patients, the antibodies from an animal source may be humanized to decrease the antigenicity, for example see WO 92/16553. The hyaluronic acid polymer is conjugated to the hapten recognized by the antibody. Suitable haptens include digoxin, digoxigenin, FITC, flourescamine, dinitrophenyl, nitrophenyl, biotin, etc. Methods for conjugation of the haptens to plysaccharides are known in the art, and exemplified in the working examples. The HA-hapten and antibody will generally be combined prior to administration, to form a complex. The complex is found to have improved activity over the unmodified polymer.

The following examples are offered by way of illustration and not by way of limitation.

EXPERIMENTAL

EXAMPLE 1
Inhibition of T cell Proliferation in Mixed Lymphocyte Reaction

An enzymatic digest of high molecular weight hyaluronic acid, having an average of six disaccharide subunits ($HA_6$) was used. This $HA_6$ preparation was tested in vitro for its ability to inhibit MHC mismatched stimulation of the T-cell response in a mixed lymphocyte reaction (MLR). The observation of a strong inhibitory effect on this system was extended to inhibition of anti-CD3 monoclonal antibody induced proliferation.

Materials and Methods

Hyaluronic acid and FITC conjugation. High molecular weight HA (sodium salt purified, from rooster comb: Sigma Chemical Co., St. Louis, Mo.) was bound to fluorescamine (Molecular Probes, Eugene, Oreg.) in a standard carbodiimide coupling procedure. Briefly, COOH groups were activated by dissolving the molecule to a final concentration of 10 mg/ml in $dH_2O$ and stirring while adding 40 mg of 1-ethyl-3-(3-dimethylaminopropyl)-carbodiimide-HCl (EDCI: Sigma). The pH of the solution was adjusted to 4.5 with 0.1 M HCl and allowed to react for 15 min. A 20 ml solution (10 mg in 0.5 ml) of fluorescamine in dH2O was then added to the HA and incubated for 2 hrs. Excess reactants were removed by extensive dialysis against PBS.

Medical grade low molecular weight HA containing six repeats of the disaccharide unit ($HA_6$) was purchased under a contract synthesis from Anika Research Inc (Woburn, Mass.). The lyophilized powder was resuspended in PBS and filter sterilized before use.

Mice and MLR. C57BL/6 and BALB/c male mice 7–8 weeks of age were purchased from Simonsen Laboratories Inc. (Gilroy, Calif.). The mice were maintained at SangStat Medical Corporation (Menlo Park, Calif.) under the provisions of the Public Health policy on humane care and use of laboratory animals. The two mouse strains have different alleles across the major histocompatibility complex, in both the Class I and Class II antigens.

| Strain | K | Ia | Ie | D |
|---|---|---|---|---|
| BALB/c | d | d | d | d |
| C57B1/6 | b | b | — | b |

One way C57BL/6 stimulator to BALB/c responder MLRs were prepared according to standard protocols. Briefly, freshly isolated C57BL/6 lymph node cells were inactivated by incubation with 25 µg/ml mitomycin C (Calbiochem, La Jolla, Calif.). After extensive washing the stimulator cells were mixed 1:1 with responder BALB/c lymph node cells and pipetted into 24 well Costar culture plates for fluorescence activated cell sorting (FACS) or 96 well flat bottomed microtiter plates for proliferation analysis.

FACS analysis. Cells from the MLR were incubated with 100 µg/ml of the fluorescamine conjugated HA (HA-FL) or 5 µg/ml of anti-CD44 antibody (IM7: Pharmingen, San Diego, Calif.) on ice for 20 min. After washing, the cells were resuspended then analyzed by flow cytometry using live gates in a FACScan and the Lysys II software (Becton Dickinson, San Jose, Calif.). This analysis of cell surface marker expression was evaluated prior to cellular activation (Day 0) and during the proliferation phase of culture (Days 4–6).

Proliferation assays. Cellular proliferation was measured by radioisotope incorporation during the MLR in the presence or absence of $HA_6$ added either at the beginning of the culture period (5 days) or 24 hrs prior to harvesting the cells. Briefly, 8 hrs prior to harvesting cells 1 µCi of $^3$H-thymidine (Amersham, Arlington Heights, Ill.) was added to each well. The cells were then harvested and isotope incorporation evaluated using a TopCount microscintillation counter (Packard, Downers Grove, Ill.).

Cell proliferation was also induced using monoclonal antibody or chemical stimulation. Normal BALB/c lymph nodes were incubated with 10 ng/ml of anti-CD3 monoclonal antibody (145.2C11: Pharmingen) or a combination of 4 ng/ml PMA (Sigma) and 400 ng/ml calcium ionophore (Sigma) in the presence or absence of $HA_6$ for 3 days. $^3$H-thymidine (Amersham) was added to the wells, and the amount of isotope incorporated evaluated as for the MLR induced proliferation.

Results

Cells from an MLR were analyzed for coordinate expression of CD44 and HA binding throughout the process of MHC allogeneic stimulation (see FIGS. 1A–1B). Results were analyzed before the initiation of proliferation, during the proliferative response, and until the culture peaked and began to die off, i.e. on Day 0, 4, 5 and 6 respectively. The mean peak fluorescence for the time points indicated are shown in FIG. 1. C57BL6 stimulation resulted in the activation of the responder BALB/c cells, and resulted in upregulation of CD44 (FIG. 1B). The data presented in FIG. 1B indicate that this increased expression of CD44 correlated with an increase in the ability to bind hyaluronic acid, shown by quantitation of binding to fluoresceinated HA. The HA-FL and CD44 antibody used in these experiments interfered with each other when attempts were made to stain the same cells with both markers at once, indicating binding to similar or adjacent determinants. The kinetics of expression indicate that there is coordinate expression of CD44 and HA binding when stimulating cells by MLR.

Addition of $HA_6$ blocked the activation of responder cells in the MLR, shown in FIG. 2. Cells were either incubated with serial dilutions of $HA_6$ over the entire 5 day period of stimulation (▲: long term), with serial dilutions of $HA_6$ added 24 hrs prior to harvesting the cells (●: End point), or without any additive (no symbol). $^3$H-thymidine was added to the culture and cellular proliferation was evaluated by isotype incorporation after 8 hrs. The mean of duplicate wells cultivated with each dilution of $HA_6$ are compared with the mean of 6 wells cultivated without HA. Only high doses (10 µg/ml) of $HA_6$ added at the start abrogated proliferation in this assay. When the $HA_6$ was added 24 hrs prior to the addition of $^3$H-thymidine, inhibition of proliferation was seen with concentrations as low as 0.5 µg/ml $HA_6$.

Two different stimulation protocols were used to determine whether the molecule was simply toxic to proliferating cells. In the first case, an anti-CD3 monoclonal antibody was used to stimulate freshly isolated lymph node cells in the presence or absence of $HA_6$. After 72 hrs of culture, $^3$H-thymidine was added and the cells harvested 8 hrs later. $HA_6$ had an inhibitory effect on this physiological stimulation, as measured by thymidine uptake. However, when PMA and ionomycin were used to stimulate the cells, no inhibition of the response was observed. This demonstrates that the inhibition is specific and that the HA preparation is not toxic to proliferating cells.

EXAMPLE 2

Inhibition of Graft Rejection

Methods

Heterotopic cardiac allagrafts. C57BL/6 mice were heavily anesthetized with metofane (methoxyflurane, Pittmann-Moore, Mundelein, Ill.), their hearts removed and the organ flushed with heparinized Ringers lactate. Heterotopic cardiac transplant to BALB/c recipients was performed according to the method of Ono and Lindsey. Treatment with 1.5 mg/Kg/day (30 µg/mouse) $HA_6$ was delivered via the tail veins in 200 µl PBS to test mice until graft rejection was complete. Graft acceptance was evaluated daily by direct palpation. Suspected rejection was confirmed by opening the peritoneal cavity of the recipient and direct observation of the graft.

Results

In vivo confirmation of the in vitro results on $HA_6$ immunosuppression was observed. BALB/C mice were transplanted with heterotopic cardiac grafts from C57BL/6 mice. This recreated many of the cellular interactions observed in the MLR. Intravenous injections of $HA_6$ alone was sufficient to prolong graft survival. Untreated control mice rejected their grafts after 9±0.7 days whereas treated mice rejected their grafts after 15.6±1.1 days. These results demonstrate that HA6 is a potent immunosuppressant when administered systemically through the course of a transplantation.

It is evident from the above results that the subject method provides a safe, effective drug to inhibit T cell activity. Disease conditions associated with undesirable T cell activity are treated by administration of hyaluronic acid. The survival time of tissue transplanted into a histoincompatible host is extended by this treatment.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of inhibiting T cell activity in graft v. host disease, said method comprising:

contacting said T cells with a formulation comprising D-glucuronic β (1–3) N-acetyl-D-glucosamine polymers of from 2 to 80 disaccharide subunits in length in an amount sufficient to inhibit said T cells;

whereby said T cell activity is inhibited.

2. A method according to claim 1, wherein about 60% by weight of said polymers are 6 disaccharide subunits in length.

3. A method of inhibiting T cell activity in graft v. host disease in a mammalian host, said method comprising:

administering systematically a formulation comprising D-glucuronic β (1–3) N-acetyl-D-glucosamine polymers of from 2 to 80 disaccharide subunits in length in an amount sufficient to inhibit said T cells;

whereby said T cell activity is inhibited.

4. A method according to claim 3, wherein said amount sufficient to inhibit said T cells is 1–25 mg of said polymers per kg of host weight.

5. A method according to claim 4, wherein about 60% by weight of said polymers are 6 disaccharide subunits in length.

6. A method of inhibiting graft rejection in a mammalian transplant recipient, the method comprising:

administering systematically to said transplant recipient a formulation comprising 1–25 mg of D-glucuronic β (1–3) N-acetyl-D-glucosamine polymers of from 2 to 80 disaccharide subunits in length per kg of host weight at daily intervals;

whereby rejection of said graft is inhibited.

7. A method according to claim 6, wherein about 60% by weight of said polymers are 6 disaccharide subunits in length.

8. A method according to claim 7, further comprising administration of a second immunosuppressive drug to said transplant recipient.

9. A method of inhibiting graft rejection in a mammalian transplant recipient, said method consisting essentially of:

administering systematically to said transplant recipient a formulation consisting of (a) 1 to 25 mg of D-glucuronic β (1–3) N-acetyl-D-glucosamine polymers per kg of host weight and (b) a physiologically acceptable solvent, at daily intervals;

whereby rejection of said graft is inhibited.

10. A method for extending the survival of an organ transplant in a recipient, said method comprising:

administering systemically to said recipient a formulation comprising D-glucuronic β (1–3) N-acetyl-D-glucosamine polymers of from 2 to 80 disaccharide subunits in length in an amount sufficient to extend the survival time of said transplant.

11. A method according to claim 10, wherein about 60% by weight of said polymers are 6 disaccharide subunits in length.

* * * * *